United States Patent [19]
Heinonen

[11] Patent Number: 6,152,131
[45] Date of Patent: Nov. 28, 2000

[54] METHOD AND APPARATUS FOR DETECTING AN EMPTY BREATHING GAS COMPARTMENT IN A PATIENT VENTILATOR

[75] Inventor: Erkki Heinonen, Helsinki, Finland

[73] Assignee: Instrumentarium Corp., Helsinki, Finland

[21] Appl. No.: 09/140,706

[22] Filed: Aug. 26, 1998

[51] Int. Cl.[7] .................................................. A61M 16/00
[52] U.S. Cl. ............... 128/204.23; 128/898; 128/204.18; 128/204.21
[58] Field of Search ................... 128/200.24, 203.12, 128/203.14, 203.24, 203.28, 204.18, 204.21, 204.22, 204.28, 205.13, 205.14, 205.15, 205.17, 205.24, 205.28, 898, 204.23

[56] References Cited

U.S. PATENT DOCUMENTS

| | | |
|---|---|---|
| 3,729,000 | 4/1973 | Bell . |
| 3,831,595 | 8/1974 | Valenta et al. ........................ 128/145.8 |
| 5,662,099 | 9/1997 | Tobia et al. ......................... 128/205.15 |
| 5,694,924 | 12/1997 | Cewers ............................... 128/205.15 |

FOREIGN PATENT DOCUMENTS

| | | |
|---|---|---|
| 678305 | 10/1995 | European Pat. Off. . |
| 776672 | 6/1997 | European Pat. Off. . |
| 798005 | 10/1997 | European Pat. Off. . |
| 835670 | 4/1998 | European Pat. Off. . |

*Primary Examiner*—Glenn K. Dawson
*Attorney, Agent, or Firm*—Andrus, Sceales, Starke & Sawall, LLP

[57] ABSTRACT

An apparatus/method for detecting an empty breathing gas compartment condition in a bellows ventilator for a patient. The apparatus includes a first sensor for measuring, during inspiration, the incoming flow of gas into a driving gas compartment located in the bellows container. The second sensor measures the pressure in the driving gas compartment. During the inspiration cycle, measurements taken by the first and second sensors are signaled to a control unit and used to determine a $\Delta V/\Delta p$ compliance value. The compliance value will be large if the bellows is movable, i.e. not in the empty breathing compartment gas condition. The compliance value is small if the empty breathing gas compartment condition exists. The compliance value, so determined, is compared with a reference compliance value in the control unit to detect the empty breathing gas compartment condition.

32 Claims, 1 Drawing Sheet

METHOD AND APPARATUS FOR DETECTING AN EMPTY BREATHING GAS COMPARTMENT IN A PATIENT VENTILATOR

BACKGROUND OF THE INVENTION

The present invention relates to apparatus for detecting an empty breathing gas compartment in a ventilator for a patient.

In medical applications, ventilators are widely used for patients unable to breath spontaneously. The inability to achieve spontaneous breathing may result from various lung diseases, or may be artificially produced as a part of a patient treatment process, such as anesthetizing a patient for surgery. The life of a patient unable to breath spontaneously depends on the proper functioning of the ventilator. Therefore, the reliability and safety of the ventilator are of central importance.

Ventilators are connected with patient airways through a breathing circuit. Through this circuit, respiratory gas is pushed into the patient's lungs by pressurizing the breathing circuit during an inspiratory phase of the breathing cycle. When a preset inspiration end condition is met, the ventilator switches automatically to an expiratory phase of the breathing cycle. In this stage, pressurization of the breathing circuit ceases and the existing pressure is released. The expiration of gas from the lungs occurs as a result of the elasticity of the patient's lungs. The ventilator repeats the breathing cycles continuously at a preset respiration rate throughout the treatment period.

Breathing circuits can be generally divided into two main categories: open circuits and circle, or closed, systems. Open circuits are favored in intensive care therapy where the inhaled gas is usually a mixture of oxygen and nitrogen and the ventilator directly feeds the breathing circuit with the gas. In anesthesia, the gas mixture also includes nitrous oxide and volatile anesthetic agents. Because the latter gases are expensive, closed systems are used to save the gas by circulating the same gas repeatedly to the patient with the removal of exhaled carbon dioxide and the supply of fresh gas to compensate for the gas consumed by the patient. The amount of the fresh gas needed is small compared to the ventilation volume of the breathing circuit. Therefore, when anesthesia ventilators are used, the fresh gas delivery is separate from the recirculating ventilation function. The fresh gas mixture intended for breathing is delivered through a separate gas supply line connected to the breathing circuit. Within the breathing system the fresh gas is mixed with the already existing gas in the breathing circuit to form the breathing gas for the patient.

In one of the most common approaches to anesthesia ventilation, the gas intended for patient breathing is pushed into the patient's lungs by pressurizing a container having two compartments separated by a moving barrier, such as a bellows. The breathing gas is on one side of the barrier. To pressurize the container, gas from a pressurized gas supply, such as oxygen or air, is provided to the other side of the barrier. This gas is commonly termed the driving gas. A driving gas control in the control unit for the ventilator regulates the driving gas flow into a driving gas compartment of the container causing the driving gas volume within the container to increase and correspondingly decreasing the volume of a breathing gas compartment containing the breathing gas. The breathing gas forced from the container is delivered through the breathing circuit to the patient's lungs. When the ventilator control unit instructs the driving gas control to release the gas from the driving gas compartment of the container, the gas under pressure within the patient's lungs flows to the breathing gas compartment of the container causing the breathing gas compartment volume to increase and the driving gas compartment volume to decrease.

For the operation of such a system, it is of central importance, that the moving barrier be located within the container at a position where it is freely moveable. One situation where this prerequisite is not fulfilled is upon emptying of the breathing gas volume from the breathing gas compartment of the container. In this situation the barrier is no longer moveable, e.g. a barrier of the bellows type is completely collapsed, and the ventilator is unable to ventilate the patient. This type of situation leads immediately to insufficient ventilation of the patient with disastrous consequences if not rapidly corrected. Therefore, detection of the foregoing situation is a primary safety measure.

One solution to detect an empty breathing gas compartment is described in U.S. Pat. No. 5,662,099. In this solution, the pressures of the breathing gas and of the driving gas, or alternatively, the differential pressure across the barrier, are measured and the fact that breathing gas compartment is empty is detected when the pressure difference exceeds a predetermined offset value. However, this solution fixes the breathing circuit pressure sensor position to a location that is near the barrier between the driving and breathing gas compartments of the container. Thus, a further, dedicated sensor is required if the patient circuit pressure is to be measured near the patient, or within the trachea of the patient. Obtaining pressure measurements from the latter location provides the ultimate primary information to control patient ventilation.

BRIEF SUMMARY OF THE INVENTION

The detection of the empty condition of the breathing gas compartment provided by the present invention employs information already existing in modern ventilators thereby freeing breathing circuit pressure measurements carried out in the ventilator for the higher priority use of patient monitoring, instead of having to, additionally, monitor the condition of the ventilator. The new detection approach is also suitable, from the practical standpoint, for use with a wide variety of ventilators and over a wide range of fresh gas flow settings encountered in anesthesia practice.

The technique of the present invention employs use of information concerning the driving gas flow, the driving gas pressure within the container, and the volume of the container. When the barrier is freely moveable within the container, upon the supply of driving gas, the driving gas pressure increase within the container represents the joint compliance of all of the container, the breathing circuit, and the patient's lungs. This joint compliance, $\Delta V/\Delta P$, is large, typically over 30 ml/cmH$_2$O, and in any case over 6 ml/cmH$_2$O.

When the movement of the barrier is stopped due to an empty breathing gas compartment, the driving gas pressure rise in the container will depend only on the container compliance and the volume of driving gas delivered into the container. As the container is rigid, the compliance is determined by gas compressibility, thus by container volume. The container volume in a ventilator is usually a constant which does not vary during the course of treatment or the life cycle of the device. Thus, in an empty breathing gas compartment condition, the compliance measured in the ventilator is essentially constant.

Ordinarily the volume of the container plus associated gas flow circuitry is about two liters. From the general ideal gas equation, pV=nRT, for a constant volume V and constant temperature T, pressure is proportional to the amount of gas n, which in the ideal gas equation is in moles. It follows that adding a quantity of gas to a given volume will increase the pressure. Thus, adding e.g. two ml of gas to a 2000 ml quantity of gas present in the volume of the container and gas flow circuitry at 1000 mbar (ambient pressure) will give a pressure in the container of 1001 mbar or 1001 cm $H_2O$. The compliance $\Delta V/\Delta p$ of the container is 2 ml/cm$H_2O$ and is the compliance exhibited when movement of the barrier is stopped due to an empty breathing gas compartment.

For recognition of the empty breathing gas compartment condition in a patient ventilator, the magnitude of this quantity as compared to the smallest values encountered in normal operation is readily apparent. Further, a recognition of the empty breathing gas compartment condition using the container compliance quantity encountered in that condition is independent of the make and size of the breathing circuit and parameters affecting pressure within the circuit.

The constancy of the container compliance whenever the empty breathing gas compartment condition is encountered is an advantage in the detection technique of the present invention. A further advantage is that this compliance value, in normally encountered operation, can be dedicated to detecting the empty breathing gas compartment condition, although a slight overlap between the empty and non-empty bellows condition compliance values may exist.

It is possible, though highly unlikely, for the technique of the present invention to erroneously identify an empty bellows condition. This may arise from the supply of fresh gas to the breathing circuit.

Compliance as seen by the ventilator is the integrated driving gas flow divided by the corresponding change in the pressure. This compliance value is subject to alteration due to the unknown fresh gas flow supply to the breathing circuit through the fresh gas supply line at the same time the driving gas is being supplied to the bellows container. The supply of fresh gas will increase the detected pressure of the driving gas and thus reduce the measured compliance value. An erroneous empty bellows detection will result when the fresh gas flow supplies the breathing circuit an amount of gas that causes a compliance measurement error that corresponds to the difference between the true compliance value and the empty breathing gas compartment compliance value.

The overall compliance is, as noted, 6 ml/cm$H_2O$ at the minimum The empty breathing gas compartment compliance value measured by the ventilator is 2 ml/cm$H_2O$. Thus the minimum difference between these two is 4 ml/cm$H_2O$. The compliance $C_1$ exhibited in the patient ventilator is $$C_1 = \Delta V_1/\Delta p \tag{1}$$

where $\Delta V_1$ is the volume of driving gas and $\Delta p$ is the pressure increment detected in the ventilator. The compliance $C_2$ arising from the supply of fresh gas is $$C_2 = \Delta V_2/\Delta p \tag{2}$$

where $\Delta V_2$ is the volume delivered by the fresh gas unit at the same time the ventilator employs the volume $\Delta V_1$.

Since gas volume is the product of gas flow and time and the same time period is employed in both flow quantities $F_{dr}$ (the driving gas flow) and $F_{fg}$ (the fresh gas flow), these quantities multiplied by time t can be substituted for the respective volume quantities $\Delta V_1$ and $\Delta V_2$.

Equation (2) can be transposed to $$F_{fg} = C_2 \times \Delta p/t \tag{3}$$

Equation (1) can be transposed to $$\Delta p = F_{dr} \times t/C_1 \tag{4}$$

Substituting equation (4) into equation (3) provides $$F_{fg} = (C_2/C_1) F_{dr} \tag{5}$$

Using the quantities $C_2$=4 ml/cm$H_2O$ and $C_1$=2 ml/cm$H_2O$ from the example given above in equation (5) indicates that the fresh gas flow $F_{fg}$ must be twice the driving gas flow for the false empty breathing gas compartment indication to occur. Such conditions do not usually occur, particularly, once the ventilator reaches the normal operating state. For example, even a typical minimum driving gas flow $F_{dr}$ of 3 liters/minutes would require a fresh gas flow rate $F_{fg}$ of 6 liters/minute to alter compliance values to an extent that would give a false indication of the empty breathing gas compartment condition. Such conditions are not likely to be encountered in practice.

Normally, the driving gas flow is many times that of the fresh gas flow. If the control unit for the ventilator does have the fresh gas flow magnitude information, it is possible to avoid false alarms by suppressing empty breathing gas container indications when the relative flows of driving gas and fresh gas is abnormal. In such cases, patient ventilation is not endangered due to the large proportion of the total ventilation arising from the fresh gas flow supply and not from the bellows.

While the expression of "compliance" has been characterized as $\Delta V/\Delta p$, it is equally possible to use the inverse $\Delta p/\Delta V$ and the term "compliance" or "compliance property" is intended to cover both relationships of $\Delta V$ and $\Delta p$. It is also obvious that instead of the integrated values $\Delta V$ and $\Delta p$, their time derivatives dv/dt and dp/dt could be used for determination of the compliance.

Further, while the obtaining of the $\Delta V$ property is described as measuring the driving gas, it would also be possible to use breathing gas volumes by employing a sensor to measure breathing gas volume.

Various other features, objects and advantages of the invention will be apparent from the following description taken together with the drawings.

BRIEF DESCRIPTION OF THE SEVERAL VIEWS OF THE DRAWING

The FIGURE of the drawing is a schematic view of an apparatus for detecting an empty breathing gas compartment condition constructed according to the present invention.

DETAILED DESCRIPTION OF THE INVENTION

Figure 1:
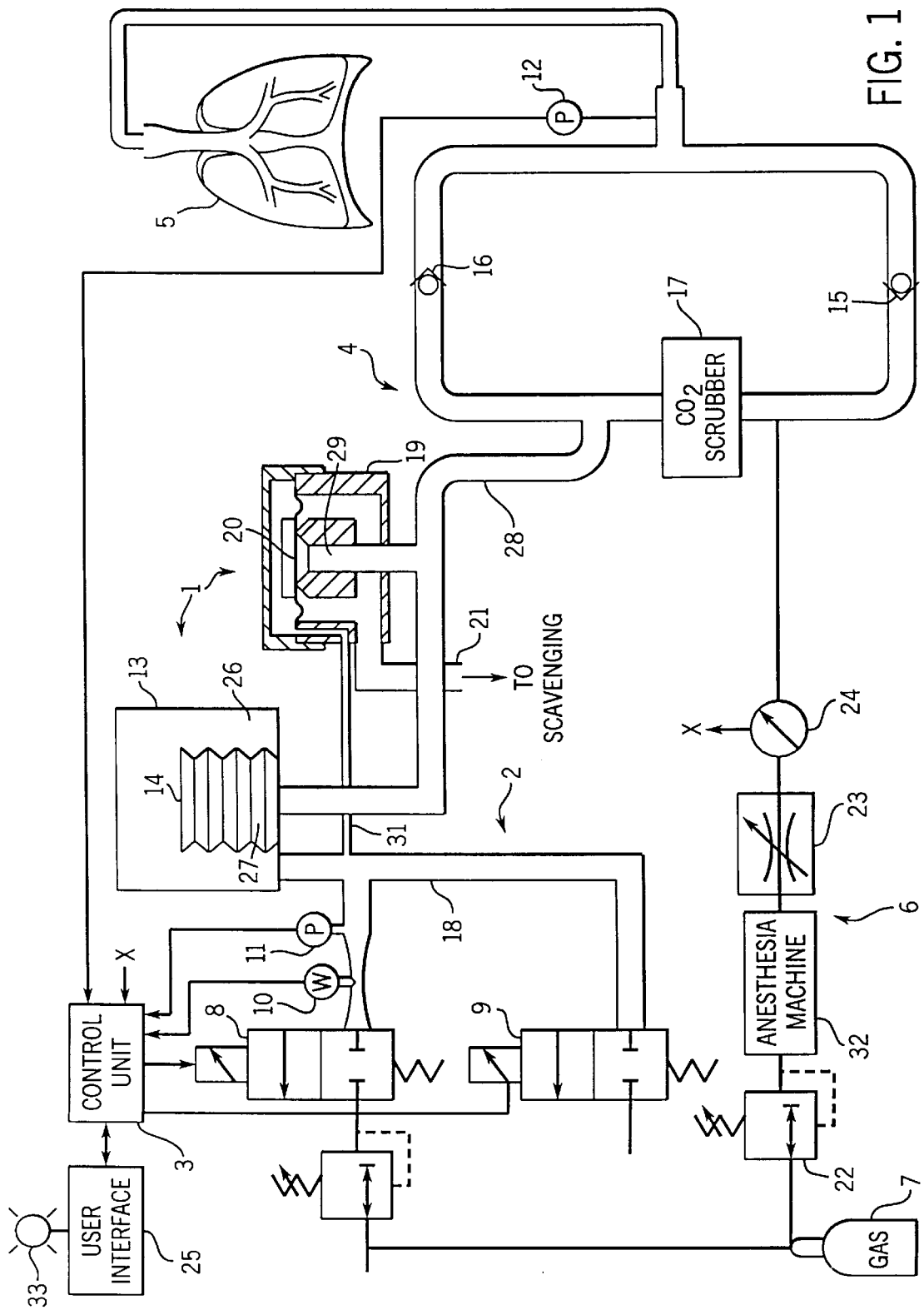

In FIG. 1, the invention is shown as comprising a ventilator including a driving gas-breathing gas interface unit 1, a driving gas control unit 2, and ventilator control unit 3. A breathing circuit 4 connects the patient lungs 5 to the driving gas-breathing gas interface unit 1. A fresh gas delivery unit 6 is connected to the breathing circuit 4 to supply breathing gas to the breathing circuit. Both the driving gas control unit 2 and the fresh gas delivery unit 6 are fed by pressurized gas from gas supply unit 7. Although FIG. 1 illustrates gas supply unit 7 as comprising only one supply tank and fresh gas delivery unit 6 for simplicity, the gas supply unit can normally include a plurality of tanks and delivery units for separate oxygen, air, and nitrous oxide delivery. Anaesthesia machine 32 provides anaesthesia agents to the fresh gas delivery unit. The driving gas control unit 2 is usually equipped with more than one gas supply unit for redundancy against failure of the gas supply unit 7 in use.

In operation, the ventilator control unit 3 controls the operation of an inspiration valve 8 and an expiration valve 9 in response to the information received from an inspiratory flow sensor 10, a driving gas compartment pressure sensor 11, a breathing circuit pressure sensor 12, and the information for the breathing cycle supplied by the user to the control unit 3 through a user interface 25.

For the inspiration portion of the breathing cycle, the ventilator control unit 3 determines a set driving gas flow value $F_{dr}$, controls the flow of driving gas with the inspiration valve 8 and receives an inspiration flow signal generated by the inspiratory flow sensor 10. The driving gas is fed through a driving gas conduit 18 into a driving gas compartment 26 of container 13. Container 13 is formed of a generally rigid material. During inspiration by the patient, the expiration valve 9, that is also in communication with the driving gas conduit 18, is closed. The driving gas flow fills the driving gas compartment 26 within the driving gas container 13, forcing a barrier 14 located within driving gas container 13, and typically formed as a bellows, to compress and empty breathing gas held within a breathing gas compartment 27 inside barrier 14 into a ventilator tube 28 that forms part of the breathing circuit 4. One way valves 15 and 16 direct the inspiration breathing gas flow from the ventilator tube 28 into the patient's lungs 5.

In accordance with the compliance of the breathing circuit 4 and the lungs 5, the pressure of the breathing circuit 4 will increase as more breathing gas is fed into the circuit 4. This pressure increase is monitored by pressure sensors 11 and 12 to keep hazardously high pressures from developing within the breathing circuit 4. Two sensors 11 and 12 are required for redundancy in the event of the failure of one of the sensors 11 or 12. Also, flow resistances within the breathing circuit 4 may cause pressure differences within the breathing circuit 4 during the course of the breathing cycle. Monitoring the pressure at different sites of the breathing circuit 4 with sensors 11 and 12 is therefore beneficial.

As shown in FIG. 1, pressure sensor 11 is positioned adjacent container 13 to monitor the pressure in driving gas compartment 26 in container 13, whereas pressure sensor 12 is positioned in the breathing circuit 4 or at the endotracheal tube for monitoring the pressure of the gas in breathing circuit 4 supplied to the patient. With sensor 12 being positioned at the distal end of the endotracheal tube within the high patient airways, a true lung pressure will be read by sensor 12.

Ventilator tube 28 also has a limb 29 connected to an exhaust valve 19. The pressure in breathing gas compartment 27 and breathing circuit 4 is thus provided to one side of exhaust valve membrane 20 in valve 19. A gas pressure equal to the pressure in driving gas compartment 26 is transmitted to the exhaust valve 19 through a tube 31 connected between driving gas conduit 18 and exhaust valve 19 and is applied to the other side of exhaust valve membrane 20. During inspiration, this latter pressure keeps exhaust valve 19 closed as the pressure within the breathing circuit 4 increases.

During the expiration cycle, the ventilator control unit 3 closes the inspiration valve 8 and opens the expiration valve 9. In doing so, the pressure is relieved from the driving gas compartment 26 of container 13. The elasticity of the patient's lungs 5 pushes the breathing gas out of the lungs 5 through the breathing circuit 4 in a flow direction defined by the one-way valves 15 and 16 back to breathing gas compartment 27 of container 13 to fill the breathing gas compartment. As the breathing gas compartment 27 is being refilled with the exhaled breathing gas, the pressure within the breathing circuit 4 will rise, forcing exhaust valve membrane 20 in exhaust valve 19 to open the valve. Any excess gas pressure over the pressure within driving gas conduit 18 is relieved through exhaust valve 19 into a gas scavenging outlet 21. The amount of gas relieved through exhaust valve 19 to scavenging outlet 21 depends on the amount of the fresh gas delivered into the breathing circuit 4 from the fresh gas delivery unit 6. The smaller the flow of incoming fresh gas is, the smaller the exhausted gas volume will be, and vice versa.

The delivery of fresh gas to breathing circuit 4 is controlled by adjusting the fresh gas flow using a pressure regulator 22 and a flow regulator 23. The actual volume of fresh gas delivered is monitored by a flow sensor 24. Flow sensor 24 may be connected to ventilator control unit 3, as shown by the connection X—X, to compensate the driving gas volume in accordance with the amount of fresh gas flow to improve the control of patient ventilation.

$CO_2$ scrubber 17 removes carbon dioxide from the exhaled breathing gases of the patient.

From the above operational description, it is apparent that the ventilator control unit 3 receives from the system all the necessary data from the system to determine an actual compliance value for the apparatus. Flow sensor 10 senses the driving gas flow delivered to the container 13. Integrating this gas flow over the time the flow was supplied gives the total volume of gas supplied to the driving gas conduit 18. Pressure sensor 11 monitors the corresponding pressure of the driving gas in container 13. The compliance is then calculated using these values. This calculated actual compliance value can then be compared with a reference compliance value that is representative of the empty breathing gas compartment condition to determine whether such a condition exists. When this condition is encountered, the control unit 3 may cease the driving gas delivery to container 13 to avoid damage by over-pressurization. Also, control unit 3 may notify the user through the user interface 25 and an alarm 33 of the empty breathing gas container condition and that corrective action is immediately required. The corrective action to be taken may include an adjustment of the fresh gas flow or the sealing of any possible leaks present within the breathing circuit 4. Such steps allow breathing gas compartment 27 of container 13 to fill with gas.

Although the detailed description illustrates the invention in connection to a ventilator system where a rising bellows represents the moving, barrier 14 separating the driving gas compartment 26 and the breathing gas compartment 27, it is obvious to one skilled in the art that the present invention could also be applied in connection with any comparable ventilation system. Some comparable ventilation systems are, e.g. those in which a hanging bellows or a bag is utilized as the moving barrier 14, both alternatives representing, in terms of the present invention, equivalent ventilation systems.

Also, while flow sensor 10 and pressure sensor 11 are shown and described in connection with driving gas conduit 18, it will be appreciated that they may be located elsewhere in the apparatus, for example in association with container 13.

Various other alternatives and embodiments are contemplated as being within the scope of the following claims particularly pointing out and distinctly claiming the subject matter regarded as the invention.

What is claimed is:

1. A method for detecting an empty breathing gas compartment condition in apparatus for ventilating a patient's lungs with breathing gas, the breathing gas compartment being located in a container and separated from a driving gas compartment by a movable barrier, the driving gas compartment being pressurizable by a driving gas to compress the breathing gas compartment to provide breathing gases to the patient, the breathing gas compartment being expandable by exhaled gases of the patient, said method comprising the steps of:

supplying driving gas to the driving gas compartment of the container;

measuring a volumetric property of one of the gases in the container;

measuring a gas pressure property indicative of that existing in the container resulting from the supply of driving gas;

determining a compliance property from the volumetric and pressure properties so measured; and ascertaining from the compliance property whether an empty breathing gas compartment condition exists in the apparatus.

2. The method of claim 1 wherein the volumetric property measuring step is further defined as measuring a volumetric property of the driving gas supplied to the container.

3. The method of claim 2 wherein the step of measuring the gas pressure property is further defined as measuring a pressure property of the driving gas.

4. The method of claim 2 wherein the step of measuring a volumetric property of the driving gas is further defined as measuring the supply of an incremental volume of driving gas to the driving gas compartment, wherein the step of measuring a gas pressure property is further defined as measuring an incremental change in the pressure of the driving gas compartment as a result of the supply of the driving gas volume, and wherein the determining step is further defined as determining the compliance property from the incremental supply volume and incremental pressure change.

5. The method of claim 4 wherein the determining step is further defined as determining the compliance property as the relationship between a change in supplied driving gas volume and the corresponding change in driving gas compartment pressure.

6. The method of claim 4 wherein the step of measuring the supply of the incremental volume of driving gas is further defined as measuring the flow of driving gas over a period of time and wherein the step of measuring the incremental change in pressure is further defined as measuring the incremental change in pressure over the same period of time.

7. The method of claim 2 wherein the steps of measuring the volumetric property and the gas pressure property are further defined as obtaining a derivative of volume with respect to time and a derivative of gas pressure with respect to time.

8. The method of claim 2 wherein the movable barrier between the driving gas compartment and breathing gas compartment is a collapsible bellows.

9. The method of claim 1 wherein the step of measuring the gas pressure property indicative of that existing in the container is further defined as measuring a gas pressure property existing in the container.

10. The method of claim 1 wherein the steps of measuring the volumetric property and the gas pressure property are further defined as obtaining a derivative of volume with respect to time and a derivative of gas pressure with respect to time.

11. The method of claim 1 wherein the ascertaining step is further defined as comparing the determined compliance property to a reference value.

12. The method of claim 11 wherein the ascertaining step is further defined as ascertaining that an empty breathing gas compartment condition exists in the apparatus when the determined compliance property bears a predetermined relationship to the reference value.

13. The method of claim 1 wherein the breathing gas compartment is in fluid communication with a breathing circuit for the patient, the breathing circuit receiving a flow of fresh gas and wherein the ascertaining step is further defined as suppressing an indication of the empty breathing gas compartment condition responsive to predetermined relative magnitudes of the driving gas flow and fresh gas flow.

14. The method of claim 1 further including the step of providing a perceptible indication of an empty breathing gas compartment condition.

15. The method of claim 1 wherein the movable barrier between the driving gas compartment and breathing gas compartment is a collapsible bellows.

16. A method for detecting a empty breathing gas compartment condition in apparatus for ventilating a patient's lungs with breathing gas, the breathing gas compartment being located in a container and separated from a driving gas compartment by a movable barrier, the driving gas compartment being pressurizable by a driving gas to compress the breathing gas compartment to provide breathing gases to the patient, the breathing gas compartment being expandable by exhaled gases of the patient, said method comprising the steps of:

supplying driving gas to the driving gas compartment of the container;

measuring the supply of an incremental volume of driving gas to the driving gas compartment;

measuring an incremental change in the pressure of the driving gas compartment as a result of the supply of the driving gas volume;

determining a compliance property from the incremental supply volume and the incremental pressure change;

comparing the determined compliance property to a reference value; and ascertaining that an empty breathing gas compartment condition exists in the apparatus when the determined compliance property bears a predetermined relationship to the reference value.

17. An apparatus for detecting an empty breathing gas compartment condition in apparatus for ventilating a patient's lungs with breathing gas, the breathing gas compartment being located in a container and separated from a driving gas compartment by a movable barrier, the driving gas compartment being pressurizable by a driving gas from a source of driving gas to compress the breathing gas compartment to provide breathing gases to the patient, the breathing gas compartment being expandable by exhaled gases of the patient, said apparatus comprising:

a first sensor for measuring a volumetric property of one of the gases in the container;

a second sensor for measuring a pressure property indicative of that existing as a result of the supply of driving gas; and means coupled to said first and second sensors for determining a compliance property from the volumetric and pressure properties so measured and for ascertaining from the compliance property whether an empty breathing gas compartment condition exists in the apparatus for ventilating a patient's lungs.

18. The apparatus of claim 17 wherein said first sensor is further defined as measuring a volumetric property of the driving gas supplied to the driving gas compartment of the container.

19. The apparatus of claim 18 wherein said second sensor is further defined as measuring a pressure property of the driving gas.

20. The apparatus of claim 18 wherein said first sensor is further defined as measuring the supply of an incremental volume of driving gas to the driving gas compartment, and wherein said second sensor is further defined as measuring an incremental change in the pressure of the driving gas compartment as a result of the supply of the driving gas volume, and wherein said determining and ascertaining means is further defined as means for determining the compliance property from the incremental volume supply and pressure change.

21. The apparatus of claim 20 wherein said determining and ascertaining means is further defined as determining the compliance property from the relationship between the incremental gas supply volume and the corresponding change in driving gas compartment pressure.

22. The apparatus of claim 20 wherein said first sensor is further defined as integrating the flow of driving gas over a period of time and wherein said second sensor is further defined as integrating the change in pressure over the same period of time.

23. The apparatus of claim 18 wherein the driving gas compartment is supplied with driving gas through a conduit from the driving gas source and wherein said first sensor is couplable to the conduit.

24. The apparatus of claim 18 further defined as apparatus for detecting an empty breathing gas compartment in ventilating apparatus in which the movable barrier between the driving gas compartment and breathing gas compartment is a collapsible bellows.

25. The apparatus of claim 17 wherein said second sensor is further defined as measuring a gas pressure property existing in the container.

26. The apparatus of claim 17 wherein said first sensor is further defined as obtaining a derivative of volume with respect to time and said second sensor is further defined as obtaining a derivative of pressure with respect to time.

27. The apparatus of claim 17 wherein said determining and ascertaining means is further defined as means for comparing the determined compliance property to a reference value.

28. The apparatus of claim 27 wherein said determining and ascertaining means is further defined as means for establishing a compliance reference value and for ascertaining that an empty breathing gas compartment condition exists in the apparatus when the determined compliance property bears a predetermined relationship to the reference value.

29. The apparatus of claim 17 wherein the breathing gas compartment is in fluid communication with a breathing circuit for the patient, the breathing circuit receiving a flow of fresh gas and wherein said apparatus is further defined as including means for suppressing an indication of the empty breathing gas compartment condition responsive to predetermined relative magnitudes of the driving gas flow and fresh gas flow.

30. The apparatus of claim 17 further including means coupled to said determining and ascertaining means for providing a perceptible indication of an empty breathing gas compartment condition.

31. The apparatus of claim 17 further defined as apparatus for detecting an empty breathing gas compartment in ventilating apparatus in which the movable barrier between the driving gas compartment and breathing gas compartment is a collapsible bellows.

32. An apparatus for detecting an empty breathing gas compartment condition in apparatus for ventilating a patient's lungs with breathing gas, the breathing gas compartment being located in a container and separated from a driving gas compartment by a movable barrier, the driving gas compartment being pressurizable by a driving gas from a source of driving gas to compress the breathing gas compartment to provide breathing gases to the patient, the breathing gas compartment being expandable by exhaled gases of the patient, said apparatus comprising:

a first sensor for measuring the supply of an incremental volume of the driving gas to the driving gas compartment of the container;

a second sensor for measuring an incremental change in the pressure of the driving gas compartment as a result of the supply of driving gas volume; and means coupled to said first and second sensor for determining a compliance property from the measured incremental volume supply and pressure change; and means for comparing the determined compliance property to a reference value and for ascertaining that an empty breathing gas compartment condition exists in the apparatus when the determined compliance property bears a predetermined relationship to the reference value.

* * * * *